US006004329A

United States Patent [19]
Myers et al.

[11] Patent Number: 6,004,329
[45] Date of Patent: Dec. 21, 1999

[54] SHAPE-ADJUSTABLE SURGICAL IMPLEMENT HANDLE

[75] Inventors: Keith Myers, Lake Forest, Calif.; Ross Bartholomew, Orem; Robert J. Todd, Salt Lake City, both of Utah; Carl Swindle, Dana Point, Calif.; Charles Weyrauch, Salt Lake City, Utah; Richard Rhee, Diamond Bar, Calif.; Jane Li, Redondo Beach, Calif.; Jerry Jackman, Tustin, Calif.; Victor Packham, Costa Mesa, Calif.

[73] Assignee: Baxter International Inc., Deerfield, Ill.

[21] Appl. No.: 09/031,789

[22] Filed: Feb. 27, 1998

Related U.S. Application Data

[63] Continuation-in-part of application No. 08/865,628, May 29, 1997.

[51] Int. Cl.⁶ ............................ A47F 13/06; A61B 17/00; A61F 11/00
[52] U.S. Cl. ............................ 606/108; 606/1; 294/19.1; 294/24
[58] Field of Search ............................ 606/1, 108, 167; 623/2, 900; 294/19.1, 24

[56] References Cited

U.S. PATENT DOCUMENTS

| 3,828,787 | 8/1974 | Anderson et al. . |
| 4,011,947 | 3/1977 | Sawyer . |
| 4,065,816 | 1/1978 | Sawyer . |
| 4,101,031 | 7/1978 | Cromie . |
| 4,182,446 | 1/1980 | Penny . |
| 4,211,325 | 7/1980 | Wright . |
| 4,512,471 | 4/1985 | Kaster et al. . |
| 4,585,453 | 4/1986 | Martin et al. . |
| 4,655,218 | 4/1987 | Kulik et al. . |
| 4,679,556 | 7/1987 | Lubock et al. ............................ 606/1 |
| 4,683,883 | 8/1987 | Martin . |
| 4,801,015 | 1/1989 | Lubock et al. . |
| 4,878,494 | 11/1989 | Phillips et al. . |
| 4,932,965 | 6/1990 | Phillips . |
| 5,089,015 | 2/1992 | Ross . |
| 5,236,450 | 8/1993 | Scott . |
| 5,360,014 | 11/1994 | Sauter et al. ............................ 623/2 |
| 5,370,685 | 12/1994 | Stevens . |
| 5,403,305 | 4/1995 | Sauter et al. ............................ 606/1 |
| 5,443,502 | 8/1995 | Caudillo et al. . |
| 5,464,421 | 11/1995 | Wortrich . |
| 5,476,510 | 12/1995 | Eberhardt et al. ............................ 623/2 |

(List continued on next page.)

FOREIGN PATENT DOCUMENTS

| 0116236 | 8/1984 | European Pat. Off. . |
| 0200419 | 5/1986 | European Pat. Off. . |
| 0103546 | 4/1988 | European Pat. Off. . |
| 0242172 | 1/1992 | European Pat. Off. . |
| 0666057 | 8/1995 | European Pat. Off. . |
| 1621912 | 2/1989 | U.S.S.R. . |
| 9212688 | 8/1992 | U.S.S.R. . |
| 9516410 | 6/1965 | WIPO . |
| 9301768 | 2/1993 | WIPO . |
| WO 93/02640 | 2/1993 | WIPO . |
| 9418909 | 9/1994 | WIPO . |
| 9514443 | 6/1995 | WIPO . |
| 9516410 | 6/1995 | WIPO . |
| 9517139 | 6/1995 | WIPO . |
| 9530386 | 11/1995 | WIPO . |

Primary Examiner—Cary O'Connor
Assistant Examiner—Navin Natnithithadha
Attorney, Agent, or Firm—Guy L. Cumberbatch; Eric K. Satermo; Monique Heyninck

[57] ABSTRACT

A multi-purpose surgical implement handle has proximal and distal ends. A gripping section is located toward the proximal end, and an attachment section is located toward the distal end. An adjusting section is interposed between the gripping section and the attachment section. The adjusting section may be bent by a human user at virtually any discrete location along the section. The adjusting section may include an increased-adjustability portion which is easier to bend than other portions of the adjusting section.

28 Claims, 6 Drawing Sheets

U.S. PATENT DOCUMENTS

| | | |
|---|---|---|
| 5,480,425 | 1/1996 | Ogilive . |
| 5,488,789 | 2/1996 | Religa et al. . |
| 5,489,296 | 2/1996 | Love et al. .................................. 623/2 |
| 5,522,884 | 6/1996 | Wright ......................................... 623/2 |
| 5,522,885 | 6/1996 | Love et al. . |
| 5,531,785 | 7/1996 | Love et al. .................................. 623/2 |
| 5,536,272 | 7/1996 | Young et al. . |
| 5,545,215 | 8/1996 | Duran . |
| 5,560,487 | 10/1996 | Starr ......................................... 206/438 |
| 5,578,076 | 11/1996 | Krueger et al. . |

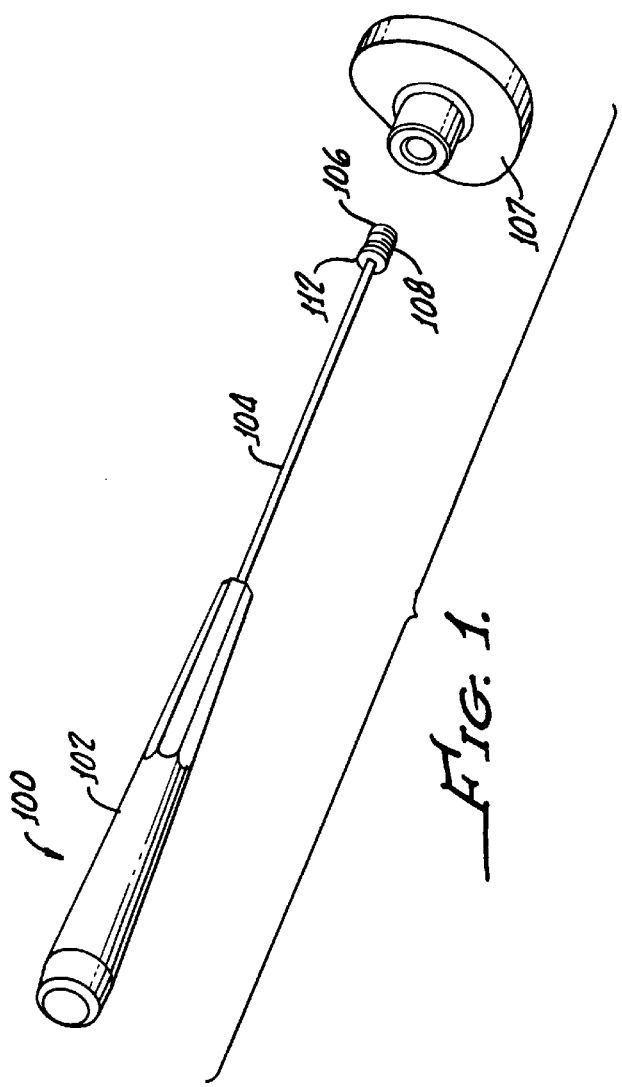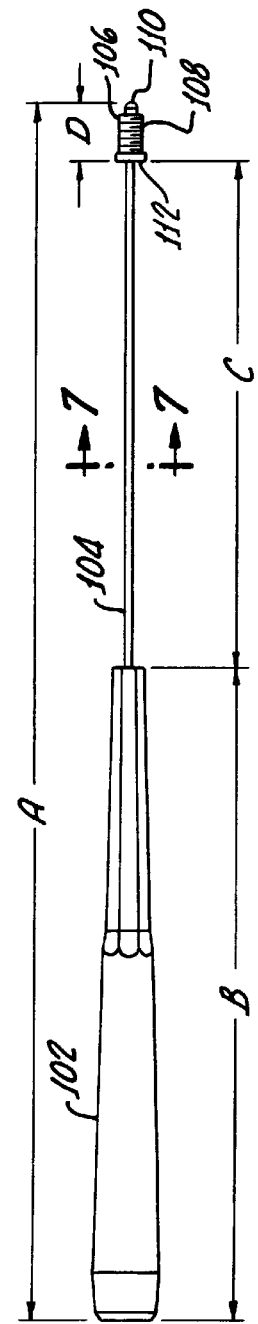

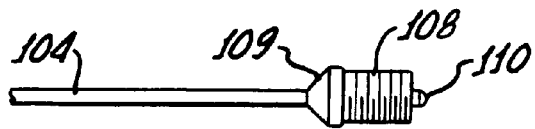
_Fig. 5._
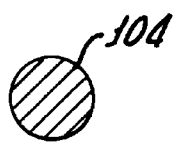      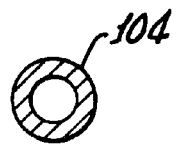
_Fig. 7A._            _Fig. 7B._
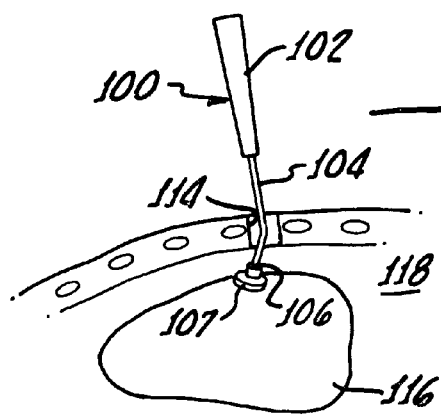
_Fig. 8._
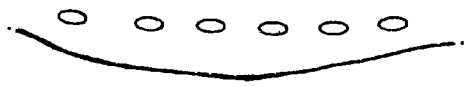

TYPE 303 STAINLESS STEEL BAR

CHEMICAL COMPOSITION

| | | | |
|---|---|---|---|
| CARBON | 0.15% MAX. | SILICON | 1.00% MAX. |
| MANGANESE | 2.00% MAX. | CHROMIUM | 17.00% TO 19.00% |
| PHOSPHORUS | 0.20% MAX. | NICKEL | 8.00% TO 10.00% |
| SULFOR | 0.15% MIN. | MOLYBDENUM | 0.60% MAX. |

| | | |
|---|---|---|
| TYPICAL MECHANICAL PROPERTIES (ANNEALED) | TENSILE STRENGTH, PSI. | 90,000 |
| | YIELD STRENGTH, PSI. | 35,000 |
| | ELONGATION, % IN 2" | 50 |
| | BRINNELL HARDNESS, 10/3000 | 160 |
| TYPICAL PHYSICAL PROPERTIES (ANNEALED) | DENSITY, LBS./CU. IN. | 0.29 |
| | MELTING RANGE, APPROX. °F | 2550-2590 |
| | SPECIFIC ELECTRICAL RESISTANCE AT ROOM TEMPERATURE, MICROHM-CENTIMETERS | 72 |
| | THERMAL CONDUCTIVITY, BTU AT 212 °F | 9.4 |
| | AVERAGE COEFFICIENT OF THERMAL EXPANSION AT 32° TO 212°F | 0.0000096 |

GOVERNMENT & INDUSTRY SPECIFICATIONS

| | |
|---|---|
| A.M.S. | 5640F |
| A.S.T.M. | A276 |
| FEDERAL | QQ-S-763c |
| MILITARY | MIL-S-7720 |
| S.A.E. | 30303F |

*Fig. 6.*

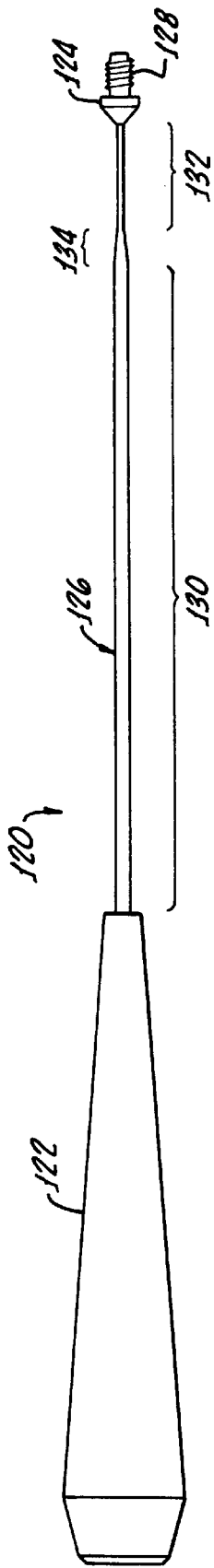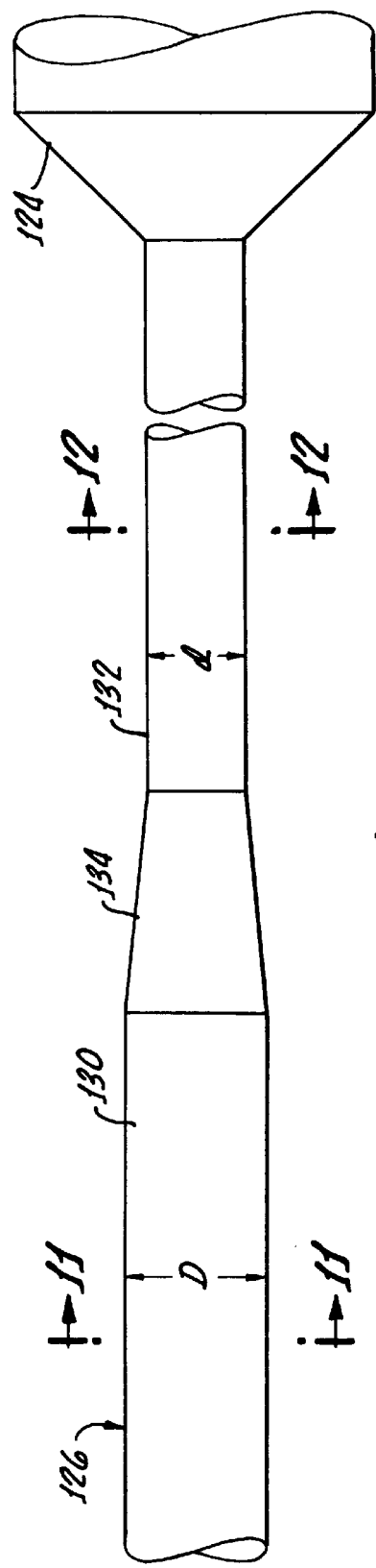

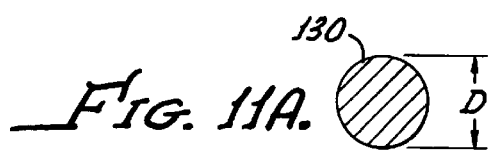
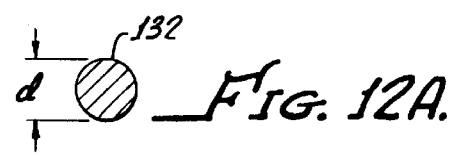
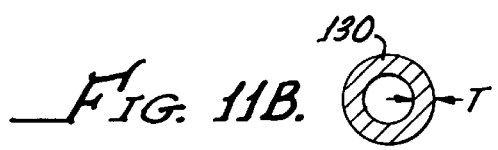
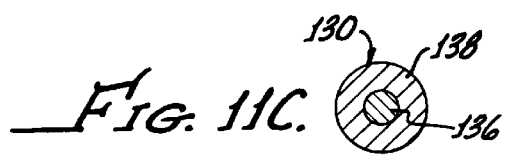
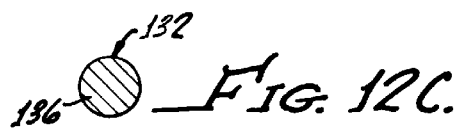
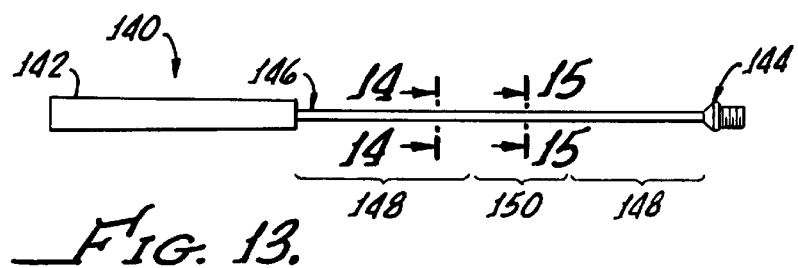
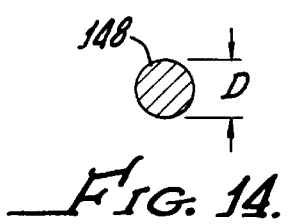
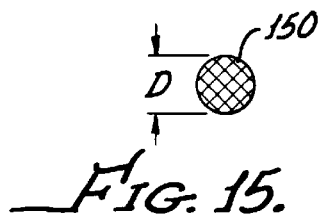

SHAPE-ADJUSTABLE SURGICAL IMPLEMENT HANDLE

CROSS-REFERENCE TO RELATED APPLICATIONS

This application for the present invention is a continuation-in-part application of Ser. No. 08/865,628 filed May 29, 1997.

FIELD OF THE INVENTION

The present invention relates to a multi-purpose surgical implement handle and particularly to a multi-purpose adjustable surgical implement handle useful in procedures where the surgical incision is small, confining or torturous.

BACKGROUND OF THE INVENTION

Surgical patients today often desire operations be performed with the least amount of intrusion into the body. Such minimally invasive procedures usually provide speedier recovery for the patient with less pain and bodily trauma, thereby reducing the medical costs and the overall disruption to the life of the patient. A minimally invasive approach also usually results in a smaller incision and, therefore, less scarring, which is an aesthetic advantage attractive to most patients.

The use of a minimally invasive approach, however, introduces new complexities to surgery thus placing a greater burden on the operating surgeon. Most notably, minimally invasive approaches drastically reduce the size of the surgical field available to the surgeon for the manipulation of tissue and for the introduction of necessary surgical instruments, such as cutting devices, clamps, prosthetic holders, and so on.

The aforesaid complexities are especially acute in connection with heart surgery. Unlike common heart surgeries performed using a full medial sternotomy, minimally invasive heart surgery offers a surgical field that may be only as large as a resected intercostal space or a transversely cut and retracted sternum. Consequently, the introduction of tools, such as prosthetic sizing elements, valve holders, annuloplasty ring holders, and other such devices, becomes a great deal more complicated.

The majority of instruments currently available to surgeons for performing minimally invasive surgeries are devices designed for use in far less restrictive surgical fields. That is, the existing instruments have characteristics which are not conducive for use in restrictive surgical fields. For example, in heart surgery, the majority of implements available to hold or retain various heart devices or tools (e.g., heart valves and annuloplasty rings) in a minimally invasive procedure either are too short to enable easy introduction of prostheses to the target site and/or have shafts which lack the necessary malleability or flexibility to enable proper orientation of the prostheses at the distal end of the shaft. Indeed, there are a number of conventional handles with shafts that require an end load of 25 pounds (lbs.) or more to bend the shaft. Furthermore, many of the existing devices have only one application, e.g., a handle for a valve-sizing template or a handle for holding a prosthetic valve, thus requiring the introduction of multiple tools into the surgical field. Examples of such prior art devices are disclosed in U.S. Pat. No. 4,679,556 to Lubock et al.; U.S. Pat. No. 5,531,785 to Love et al.; U.S. Pat. No. 5,360,014 to Sauter et al.; U.S. Pat. No. 5,403,305 to Sauter et al.; U.S. Pat. No. 5,476,510 to Eberhardt et al.; U.S. Pat. No. 5,489,296 to Love et al.; and U.S. Pat. No. 5,560,487 to Starr.

SUMMARY OF THE INVENTION

It is therefore an object of the present invention to overcome the shortcomings of the prior art by providing a multi-purpose surgical implement handle that is especially useful in minimally invasive surgical procedures.

It is a further object of the present invention to provide a surgical implement handle that has sufficient length to enable a surgeon to easily place a heart device at a target site.

It is a further object of the present invention to provide a surgical implement handle with a malleable portion that is sufficiently flexible to enable suitable orientation of the heart device for insertion in a minimally invasive procedure.

It is a further object of the present invention to provide a surgical implement handle that has multiple uses.

It is a further object of the present invention to provide a surgical implement handle that reduces the complexities of minimally invasive procedures.

It is a further object of the present invention to provide a surgical implement handle that is cost effective to produce.

These and other objects not specifically enumerated above are believed to be accomplished by a surgical implement handle according to the present invention wherein the handle includes a distal end and a proximal end. The handle has a gripping section located toward the proximal end and an attachment section located toward the distal end. The handle includes a malleable section interposed between the gripping section and the attachment section. The malleable section is sufficiently flexible to enable formation of a bend by a human user at substantially any discrete location along substantially the length of the malleable section.

According to another aspect of the invention, a shape-adjustable handle includes a gripping section disposed on a proximal end thereof, an attaching section disposed on a distal end thereof, and an adjusting section disposed between the gripping and attaching sections. The adjusting section is bendable so that the attaching section is positionable with respect to the gripping section. The attachment section may include a securing mechanism for engaging, either releasably or permanently, with a surgical implement. The adjusting section may include a main portion and an increased-adjustability portion which may be more easily bent than the main portion. For example, a surgeon may hold the gripping section in one hand and the attaching section in the other hand and may position a thumb at a discrete location along the increased-adjustability portion. The surgeon may then urge either the attaching section or the gripping section about the thumb to form a bend in the increased-adjustability section.

To be more bendable than the main portion, the increased-adjustability portion may have a smaller diameter than the main portion. Alternatively, the increased-adjustability portion may be made from material which is more malleable (or less stiff) than material from which the main portion is made. In one embodiment in which the adjusting section is tubular in cross section, the increased-adjustability portion may have a smaller wall thickness than that of the main portion. As the adjusting section is made from material which is malleable and pliable, the adjusting section is sufficiently supple to bend repeatedly without breaking or causing substantially material fatigue. The capacity of the shape-adjustable handle for adaptive change allows the handle to be readjusted to various positions during surgical procedures.

BRIEF DESCRIPTION OF THE DRAWINGS

Numerous other features and attendant advantages of the present invention shall become apparent from reference to the following description considered in conjunction with the accompanying drawings, wherein like reference numerals refer to like items and wherein:

FIG. 1 is a perspective view of a multi-purpose surgical implement handle in accordance with the present invention;

FIG. 2 is a plan view of a multi-purpose surgical implement handle in accordance with the present invention;

FIG. 5 is a plan view an attachment section useful on the multi-purpose surgical handle in accordance with the present invention;

FIG. 6 is a table of property characteristics of stainless steel as used in a preferred embodiment of the multi-purpose surgical implement handle in accordance with the present invention;

FIG. 7A is a cross-sectional view taken along line 7—7 of FIG. 2 of the surgical implement handle of the invention, illustrating a preferred embodiment of a malleable section of the handle;

FIG. 7B is a cross-sectional view similar to that of FIG. 7A, illustrating an alternative embodiment of the malleable section of the handle;

FIG. 8 is a schematic view of a minimally invasive surgical procedure, illustrating a chest cavity in cross section and a shape-adjustable handle of the invention extending through a surgical incision to a target site;

FIG. 9 is a plan view of another embodiment of a shape-adjustable handle of the invention;

FIG. 10 is an enlarged plan view of the shape-adjustable handle of FIG. 10, particularly illustrating an adjusting section including a main portion and an increased-adjustability portion;

FIG. 11A is a cross-sectional view taken along line 11—11 of FIG. 10, illustrating an exemplary embodiment of the main portion of the adjusting section of the handle;

FIG. 11B is a cross-sectional view taken along line 11—11 of FIG. 10, illustrating another exemplary embodiment of the main portion of the adjusting section;

FIG. 11C is a cross-sectional view taken along line 11—11 of FIG. 10, illustrating yet another exemplary embodiment of the main portion of the adjusting section;

FIG. 11D is a cross-sectional view taken along line 11—11 of FIG. 10, illustrating still another exemplary embodiment of the main portion of the adjusting section;

FIG. 11E is a cross-sectional view taken along line 11—11 of FIG. 10, illustrating a further exemplary embodiment of the main portion of the adjusting section;

FIG. 12A is a cross-sectional view taken along line 12—12 of FIG. 10, illustrating an exemplary embodiment of the increased-adjustability portion of the adjusting section of the handle;

FIG. 12B is a cross-sectional view taken along line 12—12 of FIG. 10, illustrating another exemplary embodiment of the increased-adjustability portion of the adjusting section;

FIG. 12C is a cross-sectional view taken along line 12—12 of FIG. 10, illustrating yet another exemplary embodiment of the increased-adjustability portion of the adjusting section;

FIG. 12D is a cross-sectional view taken along line 12—12 of FIG. 10, illustrating still another exemplary embodiment of the increased-adjustability portion of the adjusting section;

FIG. 12E is a cross-sectional view taken along line 12—12 of FIG. 10, illustrating a further exemplary embodiment of the increased-adjustability portion of the adjusting section;

FIG. 13 is a plan view of a yet another embodiment of a shape-adjustable handle of the present invention;

FIG. 14 is a cross-sectional view taken along line 14—14 of FIG. 13, illustrating a main portion of an adjusting section of the handle; and FIG. 15 is a cross-sectional view taken along line 15—15 of FIG. 13, illustrating an increased-adjustability portion of the adjusting section of the handle.

DETAILED DESCRIPTION OF THE PREFERRED EMBODIMENTS

Figure 3:
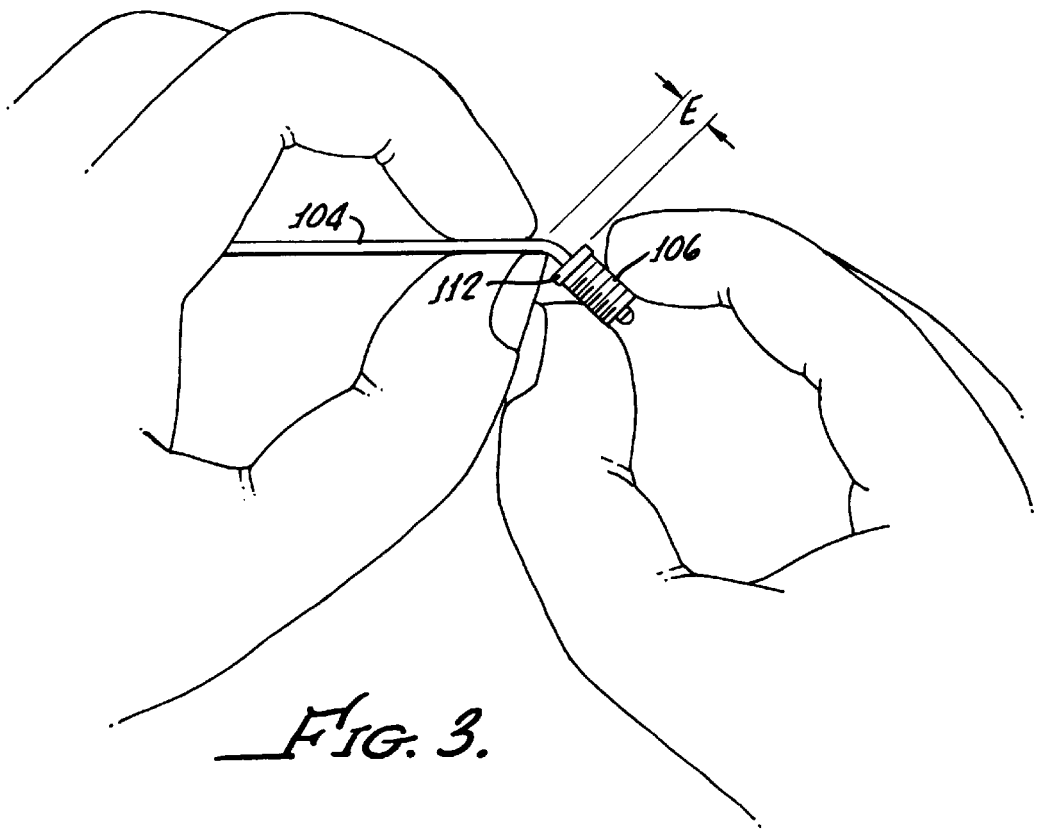
FIG. 3 is a perspective view of a multi-purpose surgical implement handle in accordance with the present invention as it is being bent by a user.

Referring to the drawing figures, and particularly FIGS. 1 and 2, a preferred embodiment of the present invention includes a handle 100 having a gripping section 102 at its proximal end, an attachment section 106 at its distal end and a malleable section 104 disposed therebetween. The handle 100 is useful for holding not only a sizing template 107 for a cardiac mitral valve but for holding any other device, e.g., a prosthetic valve sizer, a prosthetic valve, etc., as well. As such, the handle 100 is a multi-purpose tool.

The gripping section 102 has a tapered contour, narrowing from its widest portion at the proximal end of the handle 100 to its narrowest portion toward the distal end of the handle 100. The attachment section 106 is of a substantially cylindrical construction and includes a thin flat flange section 112 disposed adjacent to an externally threaded section 108 toward the distal end of the handle 100. Referring to FIG. 5, in an alternative embodiment, the attachment section 106 may include a conical shaped section 109 disposed adjacent to the externally threaded section 108. In addition, the attachment section 106 may include a circular protruding knob 110 which serves as the tip of the distal end of the handle 100.

Both the gripping section 102 and the attachment section 106 may be fabricated as an injection molded piece from a commonly known plastic or resin. In one embodiment, the external threads 108 are a 10–24 size thread, although other thread sizes are also contemplated. As will be appreciated, any device being held by the handle 100 will need internal threads of a type that will mate with the external threads 108 of the attachment section 106. It is further appreciated that the attachment section 106 may include internal, rather than external, threads and that any device being held by the handle 100 would, thus, have corresponding and complementary external threads.

The protruding knob 110 has a known function of use with at least certain prosthetic mitral valves manufactured by Baxter Healthcare Corporation. The protrusion 110 serves to exert compressive pressure in a known manner on the prosthetic mitral valve when the valve is mounted in its holder to protect leaflets of the valve while the valve is being transported to the target surgical site.

Figure 4:
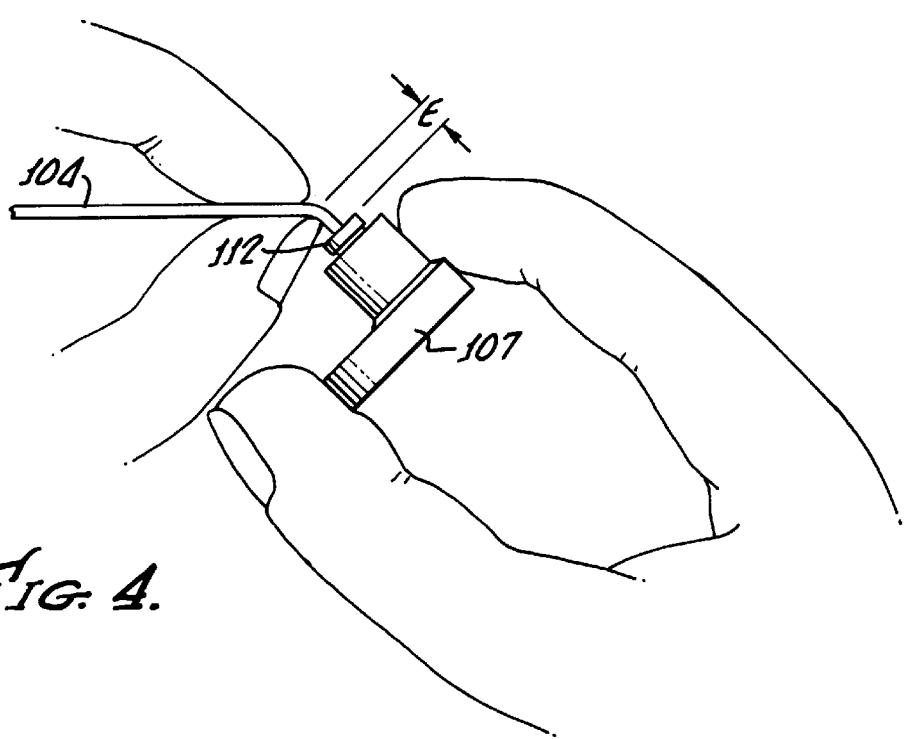
FIG. 4 is a perspective view of a multi-purpose surgical implement handle in accordance with the present invention as it is being bent by a user while the handle is holding a tool.

Referring to FIGS. 3 and 4, the malleable section 104 of the handle 100 is a wire that is sufficiently malleable or flexible to enable the surgeon to easily bend the malleable section 104 at virtually any discrete location along substantially the length of the malleable section 104, and especially very near the flange section 112 of the attachment section 106 and/or very near the gripping section 102. Moreover, as seen in FIG. 4, the malleable section 104 may be bent even while a tool such as a sizing template 107 is connected to the handle.

Referring to FIGS. 3 and 4, in one preferred embodiment, the wire is sufficiently flexible to enable the formation of a bend at a distance E from the attachment section 106 or the gripping section 102 (not shown) of approximately 0.197 inch (0.5 cm) or less. Such a wire also has a diameter within a range of 0.010 inch to 0.100 inch.

The malleable section 104 is not so flexible, however, as to be deformed or bent simply from the weight of the device being held by the handle or by inadvertent contact with peripheral objects during the surgical procedure. More specifically, the load required to bend the section 104 at a distance E of approximately 0.197 inch (0.5 cm) or less ranges from approximately 5 lbs. to approximately 10 lbs.

The malleable section 104 may be of either solid construction, as shown in FIG. 7A, or hollow construction, as shown in FIG. 7B. However, whether hollow or solid, the malleable section 104 must retain the flexibility as described.

In one preferred embodiment, the malleable section 104 is formed of a solid stainless steel wire approximately 0.050 inch in diameter from a type 302 or 303 annealed stainless-steel wire. The properties of such wire are listed in the table of FIG. 6. The load required to bend the wire at a distance E of approximately 0.197 inch (0.5 cm) from the flange is approximately 5.2 lbs. to 8.9 lbs.

Other materials, such as "memory" metals may also be suitable for the malleable section 104. Memory metals offer the additional advantage of returning to its original shape during the sterilization process. One such memory metal that is contemplated is a nickel-titanium alloy known as NITI-NOL.

The handle 100 incorporating the above-described malleable section 104 enables the surgeon to orient the device retained by the attachment device 106 in a manner that uses the least amount of space. For example, if it is desired to orient a prosthetic valve such that the valve may be inserted through a small incision and, at the same time, be properly oriented for attachment at the target site, the surgeon may do so by achieving a desired bend very near the attachment section 106 in the manner depicted in FIGS. 3 and 4. The resulting configuration enables the surgeon to introduce the valve through a small opening and avoid further manipulation of the handle while placing the valve at the target site.

Referring to FIG. 2, the overall length of the handle 100 is a length A equal to approximately 10 inches. Of the 10 inches, the gripping portion 102 has a length B of approximately 5 inches and the attachment section 106 has a length D of approximately 0.5 inch. As a result, the exposed length of the malleable section 104 has a length C of approximately 4.5 inches. It will be appreciated, however, that the wire forming the malleable section 104 is longer than the exposed length C because the wire may extend a distance into the gripping section 102 and into the attachment section 106.

Referencing FIG. 8, the length of the handle 100 must be sufficient to enable a surgeon to place the end of the handle through a surgical opening 114 and to a target site 116 in, for example, a chest cavity 118, and, at the same time, comfortably and adequately hold the gripping portion 102 of the handle. That is, the handle 100 must be of sufficient length so that the surgeon may grip the handle from above the chest opening 114 while the end of the handle is located at the target site 116 within the chest cavity 118.

It is further desired that the portion of the handle actually extending through the surgical incision and into the surgical field be the malleable section 104. This is desired as the malleable section 104 has a diameter substantially less than the gripping section 102 and, thus, the malleable section 104 affords less obstruction of the surgical field. In this regard, in a preferred embodiment, the malleable section 104 has a diameter of approximately 0.050 inch and the gripping section has a diameter of approximately 0.312 inch at the point where the gripping section 102 ends and the malleable section 104 begins. Therefore, in a preferred embodiment, the ratio of the diameter of the malleable section 104 to the smallest diameter of the gripping portion 102 is approximately 1 to 6.

A preferred embodiment of a shape-adjustable handle 120 is illustrated in FIG. 9. The handle 120 includes a gripping section 122 disposed on a proximal end thereof, an attaching section 124 disposed on a distal end thereof, and an adjusting section 126 disposed between the gripping and attaching sections 122, 124. The adjusting section 126 is bendable so that the attaching section 124 is positionable with respect to the gripping section 122, much like that shown in FIGS. 3 and 4. The attachment section 124 may include a securing mechanism 128 for engaging, either releasably or permanently, with a surgical implement. For example, as shown in FIG. 9, various interchangeable surgical implements may be threaded onto and off from the securing mechanism 128 to provide a multi-purpose surgical tool.

With additional reference to FIG. 10, the adjusting section 126 of the exemplary handle 120 may include a main portion 130 and an increased-adjustability portion 132. In accordance with the present invention, the increased-adjustability portion 132 is more bendable than the main portion 130; that is, a bend may be more easily formed in the increased-adjustability portion 132 than in the main portion 130. The adjusting section 126 of the handle 120 may also include a transition portion 134 disposed between the main portion 130 and the increased-adjustability portion 132, which will be discussed in more detail below. Although other configurations are contemplated, the exemplary embodiment illustrated in FIG. 10 shows the increased-adjustability portion 132 disposed distal to the main portion 130 and adjacent to the attaching section 124.

Although the handle 120 may be configured according to any desired specification, dimensions of an exemplary commercial embodiment of the handle 120 may include an overall length of about 15 cm to about 40 cm, a length of the gripping section 122 of about 7 cm to about 15 cm, a length of the attaching section 126 of about 1 cm to about 3 cm, and a length of the adjusting section 126 of about 10 cm to about 20 cm. Commercial dimensions of the adjusting section 126 may include a length of the main portion 130 of about 10 cm to about 15 cm, a length of the increased-adjustability portion 132 of about 2 cm to about 5 cm, and a length of the transition portion 134 of about 0.5 cm to about 1 cm.

The higher bendability of the increased-adjustability portion 132 provides surgeons with a high-leverage, stress-focusing "neck" portion of the shape-adjustable handle 120. For example, either with or without an implement in place on the attaching section 124, a surgeon may hold the gripping section 122 in one hand and the attaching section 124 in the other hand and may position a thumb at a discrete location along the increased-adjustability portion 132 (to provide a fulcrum). The surgeon may then urge the attaching section 124 about the thumb to form a bend in the increased-adjustability portion 132. Alternatively, the surgeon may urge the gripping section 122 (and the main portion 130)

about the thumb to form a bend in the increased-adjustability section 132. In either case, because the increased-adjustability portion 132 is more bendable than the main portion 130 (by being, for example, less stiff or more malleable, which will be discussed in more detail below), the adjusting section 126 will be biased, predisposed, or more likely to bend at the increased-adjustability portion 132 thereof.

If it is desired to form a bend along the main portion 130, either singularly or in addition to any bend formed in the increased-adjustability portion 132, a surgeon may position a fulcrum (such as his or her thumbs) at a desired location along the main portion 130 and urge the main portion 130 about the fulcrum. Regardless of the location of the bend or bends formed along the adjusting section 126, the attaching section 124 is positionable and adjustable with respect to the gripping section 122.

The adjusting section 126 may be made from material which is malleable and pliable. The material of the adjusting section 126 may also be sufficiently supple to bend repeatedly without breaking or causing substantially material fatigue. The shape-adjustable handle's capacity for adaptive change allows the handle to be readjusted to various positions during surgical procedures.

FIGS. 11A to 11E and 12A to 12E illustrate exemplary embodiments of the adjusting section 126 which provide the increased-adjustability portion 132 with greater flexibility, bendability, or malleability than the main portion. In FIGS. 11A and 12A, the adjusting section 126 is shown to be substantially cylindrical, with the main portion 130 having a diameter D larger than a diameter d of the increased-adjustability portion 132. For example, diameter D of the main portion 130 may be about 2 mm to 3 mm, and diameter d of the increased-adjustability portion 132 may be about 1 mm to 2 mm; in a commercial embodiment of the invention, diameter D may be about 2.3 mm and diameter d may be about 1.8 mm. In this embodiment of the handle 120, the transition portion 134 may be tapered, conical, or frustum-shaped between portions 130 and 132. Also, the main portion 130 and the increased-adjustability portion 132 may be substantially coaxial with each other.

The adjusting section 126 illustrated in FIGS. 11A and 12A is shown to be substantially unitary in construction and made from a solid piece of malleable material. In the alternative embodiment shown in FIGS. 11B and 12B, the adjusting section 126 may be made from a tubular piece of malleable material. In the tubular embodiment of the adjusting section 126, to ensure that the increased-adjustability portion 132 is more bendable or flexible than the main portion 120, the increased-adjustability section 132 may have either a diameter d less than a diameter D of the main portion 130, a wall thickness t less than a wall thickness T of the main portion 130 (and substantially equal diameters), or a combination of a smaller diameter and a thinner wall. The tubular adjusting section 126 may be formed by extrusion or molding.

Referencing FIGS. 11C and 12C, the adjusting section 126 of the handle 120 may include multiple layers of malleable material to provide portions 130 and 132 with differing malleability. For example, a central core 136 may extend the length of the adjusting section 126, and a sleeve 138 may extend along only a portion of the adjusting section 126, substantially defining the main portion 130. The core 136 may be made from material having a malleability desired for the increased-adjustability portion 132, while the sleeve 138 may be made from material having less malleability (or greater stiffness) than that of the core 136. As shown in FIG. 11C, the core 136 and the sleeve 138 may be substantially concentrically aligned.

In addition to the circular or cylindrical embodiments discussed above, the adjusting portion 126 may include a plurality of cross-sectional configurations, including elliptical or oval, as shown in FIGS. 11D and 12D, and rectilinear, as shown in FIGS. 11E and 12E. In the cross-sectional elliptical embodiment of the invention shown in FIGS. 11D and 12D, the adjusting section 126 is more bendable about the minor diameter thereof than about the major diameter thereof. Accordingly, the adjusting section 126 may be biased to be bendable about desired axes. In this regard, the adjusting section 126 may be scored or may include pre-creased segments (not shown) to facilitate or to control bending at a predetermined location(s) along the length of the adjusting section 126.

FIG. 13 illustrates an alternative embodiment of an adjustable handle 140 in accordance with the invention. Similar to the handles described above, exemplary handle 140 includes a gripping section 142, an attaching section 144, and an interdisposed adjusting section 146. The adjusting section 146 includes a main portion 148 and an increased-adjustability portion 150. The adjusting section 146 is made from malleable material and is configured such that the increased-adjustability portion 150 has a higher malleability than the main portion 148. Accordingly, the increased-adjustability portion 150 is easier to bend than the main portion 148. The increased-adjustability portion 150 may also induce the formation of a bend having a small radius of curvature. That is, bends with relatively small radii of curvature may be formed along the increased-adjustability portion 150 in an easier manner than along the main portion 148.

As shown in FIG. 13, rather than disposing the increased-adjustability portion 150 distal to the main portion 148 or adjacent to the attaching section 144, the adjusting section 146 of the exemplary handle 140 is configured with the increased-adjustability portion 150 interposed within the main portion 148. Referencing FIGS. 14 and 15, the main portion 148 has a diameter D, and the increased-adjustability portion 150 has a diameter d. To provide portions with different bending moments, diameter D may be greater than diameter d. Alternatively, the diameters D and d may be substantially equal, and the main portion 148 may be made from material having less malleability (or greater stiffness) than material from which the increased-adjustability portion 150 is made. The adjusting section 146 may be a unitary construction, or, alternatively, each of the portions 148 and 150 may be a separate piece of material connected together to form the adjusting section 146. The separate portions may be fused or molded together or may be mechanically attached. In this regard, threading or other fastening structure may be provided to engage or connect the portions 148 and 150.

Those skilled in the art will recognize that the invention may be embodied in other specific forms without departing from the spirit or essential characteristics thereof. For example, rather than being made from malleable material, the adjusting portion 126 may be comprised of a plurality of articulated sections connected by pivoting joints and a cable. In this configuration, the adjusting portion 126 may be bend as desired and then the cable may be tensioned to hold the articulated sections in place. The foregoing is intended, therefore, to be illustrative and not restrictive, and the scope of the invention is defined by the following claims. All versions which are equivalent to the claims are therefore intended to be embraced by such claims.

What is claimed is:

1. A handle for holding an implement, comprising:

a gripping section;

an attaching section to which The implement is mountable; and an adjusting section disposed between said gripping section and said attachment section, said adjusting section being bendable to allow said attachment section to be positioned with respect to said gripping section;

said adjusting section including a main portion and an increased-adjustability portion, said increased-adjustability portion being more bendable than said main portion, and wherein said adjusting section is re-adjustable such that multiple bends are formable therein.

2. A handle as set forth in claim 1, wherein said adjusting section is made from malleable material;

said increased-adjustability portion having a higher malleability than said main portion.

3. A handle as set forth in claim 1, wherein said increased-adjustability portion has smaller physical dimensions than said main portion.

4. A handle as set forth in claim 3, wherein said adjusting section is cylindrical;

said main portion and said increased-adjustability portion each having a diameter, said diameter of said increased-adjustability portion being less than said diameter of said main portion.

5. A handle as set forth in claim 3, wherein said adjusting section is tubular;

said main portion and said increased-adjustability portion each having a wall thickness, said wall thickness of said increased-adjustability portion being less than said wall thickness of said main portion.

6. A handle as set forth in claim 1, wherein said increased-adjustability portion is adjacent to said attachment section.

7. A handle as set forth in claim 1, wherein at least one of said portions of said adjustable section is solid.

8. A handle as set forth in claim 1, wherein at least one of said portions of said adjustable section is tubular.

9. A handle as set forth in claim 1, wherein said main portion and said increased-adjustability portion are substantially coaxial.

10. A handle as set forth in claim 1, wherein said adjusting section further includes a transition portion disposed between said main portion and said increased-adjustability portion.

11. A handle as set forth in claim 10, wherein said adjusting section is cylindrical;

said main portion and said increased-adjustability portion each having a diameter, said diameter of said increased-adjustability portion being less than said diameter of said main portion; and said transition portion being conical.

12. A handle as set forth in claim 11, wherein said adjusting portion is unitarily solid.

13. A handle as set forth in claim 1, wherein said attachment section includes a securing mechanism for releasably engaging with a surgical implement.

14. A handle as set forth in claim 1, wherein said adjusting section has a non-circular cross-section.

15. A handle as set forth in claim 14, wherein said non-circular cross-section is more flexible about at least one bending plane at least one other bending plane.

16. A handle as set forth in claim 15, wherein said adjusting section has an elliptical cross-section.

17. A handle for holding an implement, comprising:

a gripping section;

an attaching section to which the implement is mountable; and and adjusting section disposed between said gripping section and said attachment section, said adjusting section being bendable to allow said attachment section to be positioned with respect to said gripping section;

said adjusting section including a main portion and an increased-adjustability portion, said increased-adjustability portion being more bendable than said main portion, and wherein said adjusting section further includes a transition portion disposed between said main portion and said increased adjustability portion.

18. A handle as set forth in claim 17, wherein said adjusting section is cylindrical;

said main portion and said increased-adjustability portion each having a diameter said diameter of said increased-adjustability portion being less than said diameter of said main portion; and said transition portion being conical.

19. A handle as set forth in claim 18, wherein said adjusting portion is unitarily solid.

20. A handle as set forth in claim 17, wherein said adjusting section is made from a malleable material;

said increased-adjustability portion having a higher malleability than said main portion.

21. A handle as set forth in claim 17, wherein said adjusting section is tubular;

said main portion and said increased-adjustability portion each having a wall thickness, said wall thickness of said increased-adjustability portion being less than said wall thickness of said main portion.

22. A handle as set forth in claim 17, wherein said increased-adjustability portion is adjacent to said attachment section.

23. A handle as set forth is claim 17, wherein at least one of said portions of said adjustable section is solid.

24. A handle as set forth in claim 17, wherein at least one of said portions of said adjustable section is tubular.

25. A handle as set forth in claim 17, wherein said main portion and said increased-adjustability portion are substantially coaxial.

26. A handle as set forth in claim 17, wherein said adjusting section has a non-circular cross-section.

27. A handle as set forth in claim 26, wherein said non-circular cross section is more flexible about at least one bending plane than at least one other bending plane.

28. A handle as set forth in claim 27, wherein said adjusting section has an elliptical cross-section.

* * * * *